(12) United States Patent
Dupuis

(10) Patent No.: US 6,613,315 B1
(45) Date of Patent: Sep. 2, 2003

(54) COSMETIC COMPOSITION COMPRISING AT LEAST ONE NONIONIC AMPHIPHILIC ASSOCIATIVE POLYURETHANE AND AT LEAST ONE NONIONIC POLYMER WITH FATTY CHAINS

(75) Inventor: Christine Dupuis, Paris (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/402,801

(22) PCT Filed: Dec. 23, 1998

(86) PCT No.: PCT/FR98/02866

§ 371 (c)(1),
(2), (4) Date: Dec. 22, 1999

(87) PCT Pub. No.: WO99/40893

PCT Pub. Date: Aug. 19, 1999

(30) Foreign Application Priority Data

Feb. 13, 1998 (FR) .............................. 98 01777

(51) Int. Cl.⁷ ............................ A61K 7/06; A61K 47/30
(52) U.S. Cl. ............... 424/70.17; 424/70.1; 424/70.11; 424/70.13; 424/70.15; 424/70.16; 514/772; 514/772.3; 514/772.4; 514/772.5; 514/772.6; 514/772.7; 514/777; 514/778; 514/781
(58) Field of Search ............................ 424/70.1, 70.11, 424/70.13, 70.15, 70.17, 70.19, 70.21, 70.22, 70.27, 70.31, 70.16; 514/772, 772.3, 772.4, 772.6, 772.5, 772.7, 777, 778, 781

(56) References Cited

U.S. PATENT DOCUMENTS

| | | | |
|---|---|---|---|
| 4,155,892 A | * 5/1979 | Emmons et al. | 524/507 |
| 4,833,225 A | 5/1989 | Schaefer et al. | 528/28 |
| 4,891,166 A | 1/1990 | Schaefer et al. | 554/39 |
| 5,294,692 A | 3/1994 | Barron et al. | 526/301 |
| 5,344,643 A | 9/1994 | Thiel et al. | 424/70.11 |
| 5,478,562 A | 12/1995 | Cauwet et al. | 424/401 |
| 5,534,265 A | * 7/1996 | Fowler et al. | 424/489 |
| 5,538,717 A | 7/1996 | La Poterie | 424/61 |
| 5,661,118 A | 8/1997 | Cauwet et al. | 510/126 |

FOREIGN PATENT DOCUMENTS

| | | |
|---|---|---|
| DE | 37 05 121 | 9/1988 |
| DE | 37 19 086 | 10/1988 |
| DE | 44 38 846 | 5/1996 |
| EP | 0 282 720 | 9/1988 |
| EP | 0 339 712 | 11/1989 |
| EP | 0 412 705 | 2/1991 |
| EP | 0 415 705 | 3/1991 |
| EP | 0 530 974 | 3/1993 |
| EP | 0 555 155 | 8/1993 |
| EP | 0 617 607 | 10/1994 |
| EP | 0 637 600 | 2/1995 |
| EP | 0 648 485 | 4/1995 |
| EP | 0 714 654 | 6/1996 |
| EP | 0 745 373 | 12/1996 |
| EP | 0 824 914 | 2/1998 |
| FR | 2 733 910 | 11/1996 |
| FR | 2 738 835 | 3/1997 |
| FR | 2 750 047 | 12/1997 |
| FR | 2 758 262 | 7/1998 |
| WO | 97/02325 | * 1/1997 |
| WO | 98/00494 | * 1/1998 |

OTHER PUBLICATIONS

Zeying Ma et al., "Phase Behaviors and Film Properties of Dispersions and Coatings Containing Associative and Conventional Thickeners", Journal of Applied Polymer Science, vol. 49, 1993, pp. 1509–1527.
English language Derwent Abstract of DE 37 05 121.
English language Derwent Abstract of DE 44 38 846.
English language Derwent Abstract of EP 0 637 600.
English language Derwent Abstract of EP 0 714 654.
English language Derwent Abstract of EP 0 745 373.
English language Derwent Abstract of FR 2 738 835.
English language Derwent Abstract of FR 2 733 910.
English language Derwent Abstract of FR 2 750 047.
English language Derwent Abstract of FR2 758 262.

* cited by examiner

Primary Examiner—Jose' G. Dees
Assistant Examiner—Frank Choi
(74) Attorney, Agent, or Firm—Finnegan, Henderson, Farabow, Garrett & Dunner, L.L.P.

(57) ABSTRACT

The invention concerns cosmetic compositions containing, in a cosmetically acceptable medium, as thickening system: (A) at least a non-ionic associative polyurethane and (B) at least a non-ionic polymer comprising at least a fatty chain.

17 Claims, No Drawings

COSMETIC COMPOSITION COMPRISING AT LEAST ONE NONIONIC AMPHIPHILIC ASSOCIATIVE POLYURETHANE AND AT LEAST ONE NONIONIC POLYMER WITH FATTY CHAINS

This application is a 371 of PCT/FR98/02866, filed on Dec. 23, 1998.

The present invention relates to cosmetic compositions containing a novel thickening system of aqueous media based on associative polyurethanes and fatty chain nonionic polymers, as well as to their use in particular as leave-in haircare gels or styling gels.

The thickening and/or gelation of aqueous media with polymers has been an important subject of cosmetic research for a long time. The production of an advantageous thickening effect with a water-soluble polymer generally assumes a high molar mass and a large hydrodynamic volume. The gelation of an aqueous medium is then considered as being the result of a three-dimensional polymer network obtained by crosslinking linear polymers or by copolymerizing bifunctional and polyfunctional monomers. However, the use of such polymers of very high molar mass poses a certain number of problems, such as the relatively unpleasant texture and the difficulty in spreading the gels obtained.

One advantageous approach consists in using, as thickeners, polymers capable of reversibly self-associating or of associating with other molecules or particles. This physical association gives rise to thixotropic or rheofluidizing macromolecular systems, i.e. systems whose viscosity depends on the shear forces to which they are subjected.

Such polymers capable of reversibly self-associating or of associating with other molecules are known as "associative polymers". The forces of interaction in play can be very different in nature, for example of electrostatic nature, of hydrogen bonding type or hydrophobic interactions.

One specific case of associative polymers is amphiphilic polymers, i.e. polymers comprising one or more hydrophilic portions which make them soluble in water, and one or more hydrophobic zones via which the polymers interact and self-assemble or assemble with other molecules.

It is known practice to prepare hair compositions in gel form using, as thickening system, such associative amphiphilic polymers, in combination with surfactants. It is thought that the advantageous rheological properties of the gels thus obtained are due to the formation of mixed micelles containing the surfactants and the hydrophobic portions of the amphiphilic polymers, these micelles constituting a multitude of physical crosslinking points.

However, these compositions based on associative polymers and surfactants do not always have the desired cosmetic properties. Thus, the presence of surfactants, even in small amounts, can bring about an undesirable change in the cosmetic properties of the said compositions, such as the properties of application or of feel after drying. Moreover, in particular in the sector of leave-in haircare or styling gels, it is important to be able to distribute the product uniformly over the entire head of hair so as to avoid excessive loads and the cosmetic defects resulting therefrom.

It has now been discovered that it is possible to obtain a good thickening, or even gelling, effect and advantageous cosmetic properties by combining associative nonionic polyurethanes with nonionic polymers comprising at least one unit containing a fatty chain.

The gel obtained by the combination of these two types of polymer has a very melting texture and is pleasant to apply. The final feel on dried hair is more pleasant and less laden. The gel moreover has excellent styling power.

One subject of the present invention is thus a cosmetic composition comprising at least one associative nonionic polyurethane in combination with at least one nonionic polymer comprising at least one unit containing a fatty chain.

Another subject of the present invention is the use of the combination of at least associative nonionic polyurethane and at least one nonionic polymer comprising at least one unit containing a fatty chain as a thickening system for cosmetic compositions.

A third subject of the invention is a cosmetic process for treating the hair using a cosmetic composition obtained by combining at least one nonionic associative polyurethane and at least one nonionic polymer comprising at least one unit containing a fatty chain.

Other subjects will become apparent on reading the description and the examples which follow.

The cosmetic compositions in accordance with the invention are essentially characterized in that they contain, in a cosmetically acceptable medium, (A) at least one amphiphilic nonionic associative polyurethane corresponding to the general formula

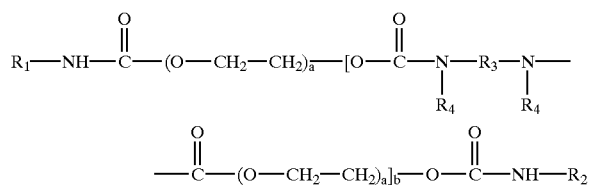

(I)

in which at least one of the residues $R_1$ and $R_2$ represents a $C_8$–$C_{18}$ higher alkyl group and the other, where appropriate, represents a $C_1$–$C_6$ lower alkyl group, $R_3$ represents a $C_4$–$C_{36}$, preferably $C_6$–$C_{10}$, hydrocarbon-based radical, $R_4$ represents a hydrogen atom or a $C_1$–$C_6$ alkyl radical, preferably a hydrogen atom, a ranges, independently, from 90 to 600, and b is from 1 to 4, and (B) at least one nonionic polymer comprising at least one unit containing a fatty chain and which is other than the polyurethane of formula (I).

According to the invention, the expression "$C_1$–$C_6$ lower alkyl group" means an alkyl group containing a linear or branched chain comprising from 1 to 6 carbon atoms, such as methyl, ethyl, n-propyl, n-butyl, n-pentyl and n-hexyl radicals, as well as the corresponding branched isomers.

In accordance with the invention, the $C_8$–$C_{18}$ higher alkyl groups denote alkyl groups containing a linear or branched chain comprising from 8 to 18 carbon atoms, such as octyl, nonyl, decyl, undecyl, dodecyl, tridecyl, tetradecyl, pentadecyl, hexadecyl, heptadecyl and octadecyl radicals.

In one preferred embodiment, only one of the α,ω-alkyl radicals $R_1$ and $R_2$ of the polymer of formula (I) represents a $C_8$–$C_{18}$ higher alkyl group and the other represents a $C_1$–$C_6$ lower alkyl group.

A particularly recommended associative polyurethane of the present invention is that in which one of the groups $R_1$ and $R_2$ represents an octadecyl radical and the other represents a methyl group.

The associative polyurethanes used in the compositions of the present invention are used in the form of an aqueous solution or suspension optionally containing a certain amount of soluble starch. This starch can be any starch extracted from natural sources, such as wheat starch, cornstarch, rice starch, potato starch, etc. and which has been chemically, enzymatically or microbiologically modified so as to be soluble in water.

A preferred polymer is sold by the company Rohm & Haas under the name Acrysol 46. It is a polyurethane obtained by condensation of hexamethylene diisocyanate and polyethylene glycol, and bearing, on average, a methyl residue and an octadecyl residue at its ends, respectively. This polymer is in the form of an aqueous solution containing 15% by weight of polyurethane active material also containing 3–5% of an enzymatically modified starch matrix.

According to the present invention, the nonionic polymers comprising at least one fatty chain, which are used as component (B), are preferably chosen from:

(1) celluloses modified with groups comprising at least one $C_{8-22}$ fatty chain, for example hydroxyethylcellulose modified with groups comprising at least one $C_{8-22}$ fatty chain. Such a product is, for example, Natrosol Plus Grade 330 ($C_{16}$ alkyl chains), sold by the company Aqualon, or Bermocoll EHM 100 sold by the company Berol Nobel; or celluloses modified with alkylphenyl polyalkylene glycol ether groups, such as the product Amercell Polymer® HM-1500 sold by the company Amerchol;

(2) hydroxypropyl guars modified with groups comprising at least one $C_{8-22}$ fatty chain, such as the product Esaflor® HM 22 sold by the company Lamberti, and the products Miracare® XC95-3 and RE205-1 sold by the company Rhône-Poulenc;

(3) copolymers of vinylpyrrolidone and of hydrophobic monomers containing a $C_{8-22}$ fatty chain, such as, for example, the products Antaron® V216, Antaron® V220, Ganex® V261 and Ganex® V220, sold by the company I.S.P.;

(4) copolymers of $C_{1-6}$ alkyl methacrylates or acrylates and of amphiphilic monomers comprising at least one $C_{8-22}$ fatty chain, such as, for example, the oxyethylenated methyl methacrylate/stearyl acrylate copolymer sold by the company Goldschmidt under the name Antil® 208;

(5) copolymers of hydrophilic methacrylates or acrylates and of hydrophobic monomers comprising at least one $C_{8-22}$ fatty chain, such as, for example, a copolymer of polyethylene glycol methacrylate and of lauryl methacrylate, such as the product 470/66 sold by the company National Starch;

(6) polyurethanes comprising at least one unit containing a fatty chain, which are other than the polyurethanes of formula (I).

According to the invention, the associative polyurethanes and the nonionic polymers containing fatty chains are used in amounts which are sufficient to obtain satisfactory thickening or gelation of the aqueous medium.

An amount of associative polyurethanes of between 0.1 and 10% by weight and preferably between 0.5 and 5% by weight, expressed as active material and relative to the total weight of the composition, is recommended in particular.

In the compositions of the present invention, the nonionic polymers comprising at least one unit containing a fatty chain are present in a proportion of from 0.01 to 10% by weight, preferably in a proportion of from 0.1 to 5% by weight, of active material relative to the total weight of the composition.

In the present invention, the ratio of the said nonionic associative polyurethane (A) of formula (I) to the said nonionic polymer comprising at least one unit containing a fatty chain (B) is preferably within the range from 90/10 to 10/90.

The cosmetically acceptable medium preferably consists of water and can also contain cosmetically acceptable solvents, for example lower monoalcohols such as ethanol or isopropanol, glycols such as ethylene glycol, glycol ethers such as the alkyl ethers of ethylene glycol or of diethylene glycol, or alternatively fatty acid esters, all of these solvents being used alone or in the form of a mixture.

The haircare or styling gels can also contain one or more additives usually used in such hair compositions. Mention may be made, for example, of fragrances, dyes, preserving agents, sunscreens, vitamins, pH regulators, etc. It is clearly understood that the choice of these compounds should take into account possible interactions with the thickening system. A person skilled in the art will take care to ensure that the addition of these additives will not have an unfavourable influence on the advantageous properties of the compositions obtained by means of the present invention.

One preferred cosmetic process for treating the hair, according to the invention, consists in applying and homogeneously distributing the compositions defined above on the hair and in drying the hair thus treated without rinsing it.

The examples which follow are intended to illustrate the invention without thereby being limiting in nature.

EXAMPLE 1

A gel having the composition below was prepared:

| | |
|---|---|
| Acrysol 46 | 2% active material |
| 470/66* | 2% active material |
| demineralized water | qs 100 g |

*The polymer 470/66 (sold by the company National Starch) is a copolymer of polyethylene glycol methacrylate and of lauryl methacrylate as an aqueous 39.2% solution.

EXAMPLE 2

A gel having the composition below was prepared:

| | |
|---|---|
| Acrysol 46 | 3% active material |
| Amercell Polymer HM 1500* | 2% active material |
| demineralized water | qs 100 g |

*The polymer Amercell Polymer HM 1500 is nonoxynylhydroxyethylcellulose sold by the company Amerchol.

EXAMPLE 3

A gel having the composition below was prepared:

| | |
|---|---|
| Acrysol 46 | 4% active material |
| Bermodol Pur 2130* | 3% active material |
| demineralized water | qs 100 g |

*The polymer Bermodol Pur 2130 (sold by the company Berol Nobel) is a modified polyurethane (as an aqeuous 25% solution).

It is clearly understood that the description hereinabove is given for purely illustrative purposes and without any implied limitation, and that variants or modifications may be applied thereto in the context of the present invention.

What is claimed is:

1. A cosmetic composition comprising in a cosmetically acceptable medium, (A) at least one nonionic amphiphilic associative polyurethane corresponding to formula (I):

$$R_1-NH-\overset{O}{\overset{\|}{C}}-(O-CH_2-CH_2)_{\overline{a}}-[O-\overset{O}{\overset{\|}{C}}-\underset{R_4}{\overset{|}{N}}-R_3-\underset{R_4}{\overset{|}{N}}-\overset{O}{\overset{\|}{C}}-(O-CH_2-CH_2)_a]_b-O-\overset{O}{\overset{\|}{C}}-NH-R_2 \quad (I)$$

in which
- at least one of the radicals $R_1$ and $R_2$ is a higher alkyl group having 8 to 18 carbons,
- $R_3$ is a hydrocarbon-based radical having from 4 to 36 carbons,
- $R_4$ is chosen from hydrogen and $C_1$–$C_6$ alkyl radicals,
- a ranges, independently, from 90 to 600, and
- b ranges from 1 to 4, and (B) at least one nonionic polymer comprising at least one unit containing a fatty chain and which is other than the polymer of formula (I).

2. The composition according to claim 1, wherein $R_3$ has from 6 to 10 carbons.

3. The composition according to claim 1, wherein $R_4$ is hydrogen.

4. The composition according to claim 1, wherein one of the groups $R_1$ and $R_2$ is a higher alkyl group having 8 to 18 carbons and the other group is a lower alkyl group having 1 to 6 carbons.

5. The composition according to claim 4, wherein the higher alkyl group is an octadecyl group and the lower alkyl group is a methyl group.

6. The composition according to claim 5, wherein the at least one nonionic amphiphilic associative polyurethane of formula (I) having the octadecyl group as the higher alkyl group and the methyl group as the lower alkyl group is obtained by polycondensation of hexamethylene diisocyanate and polyethylene glycol.

7. The composition according to claim 1, wherein the at least one nonionic amphiphilic associative polyurethane of formula (I) is in a solution or suspension in water, which also contains chemically, enzymatically or microbiologically modified soluble starch.

8. The composition according to claim 1, wherein the at least one nonionic polymer comprising at least one unit containing a fatty chain is chosen from:
  (1) celluloses modified with groups comprising at least one $C_{8-22}$ fatty chain;
  (2) hydroxypropyl guars modified with groups comprising at least one $C_{8-22}$ fatty chain;
  (3) copolymers of vinylpyrrolidone and of hydrophobic monomers containing a $C_{8-22}$ fatty chain;
  (4) copolymers of $C_{1-6}$ alkyl methacrylates or acrylates and of amphiphilic monomers comprising at least one $C_{8-22}$ fatty chain;
  (5) copolymers of hydrophilic methacrylates or acrylates and of hydrophobic monomers comprising at least one $C_{8-22}$ fatty chain; and
  (6) polyurethanes comprising at least one unit containing a fatty chain, which is other than the nonionic amphiphilic associative polyurethane of formula (I).

9. The composition according to claim 8, wherein the cellulose modified with groups comprising at least one $C_{8-22}$ fatty chain are chosen from:

(1) hydroxyethylcelluloses modified with groups comprising at least one $C_{8-22}$ fatty chain; and
  (2) celluloses modified with alkylphenyl polyalkylene glycol ether groups.

10. The composition according to claim 1, wherein the at least one nonionic amphiphilic associative polyurethane of formula (I) is present in an amount of from 0.1 to 10% by weight of active material relative to the total weight of the composition.

11. The composition according to claim 10, wherein the at least one nonionic amphiphilic associative polyurethane of formula (I) is present in an amount of from 0.5 to 5% by weight of active material relative to the total weight of the composition.

12. The composition according to claim 1, wherein the at least one nonionic polymer comprising at least one unit containing a fatty chain is present in an amount of from 0.01 to 10% by weight of active material relative to the total weight of the composition.

13. The composition according to claim 12, wherein the at least one nonionic polymer comprising at least one unit containing a fatty chain is present in an amount of from 0.1 to 5% by weight of active material relative to the total weight of the composition.

14. The composition according to claim 1, wherein the weight ratio of the nonionic amphiphilic associative polyurethane of formula (I) and the nonionic polymer comprising at least one unit containing a fatty chain ranges from about 90/10 to 10/90.

15. A leave-in haircare gel or styling gel comprising, in a cosmetically acceptable medium:

(A) at least one nonionic amphiphilic associative polyurethane corresponding to formula (I):

$$R_1-NH-\overset{O}{\overset{\|}{C}}-(O-CH_2-CH_2)_{\overline{a}}-[O-\overset{O}{\overset{\|}{C}}-\underset{R_4}{\overset{|}{N}}-R_3-\underset{R_4}{\overset{|}{N}}-\overset{O}{\overset{\|}{C}}-(O-CH_2-CH_2)_a]_b-O-\overset{O}{\overset{\|}{C}}-NH-R_2 \quad (I)$$

in which
- at least one of the radicals $R_1$ and $R_2$ is a higher alkyl group having 8 to 18 carbons,
- $R_3$ is a hydrocarbon-based radical having from 4 to 36 carbons,
- $R_4$ is chosen from hydrogen and $C_1$–$C_6$ alkyl radicals,
- a ranges, independently, from 90 to 600, and
- b ranges from 1 to 4, and (B) at least one nonionic polymer comprising at least one unit containing a fatty chain and which is other than the polymer of formula (I).

16. A process for thickening a cosmetic composition comprising adding to the composition (A) at least one nonionic amphiphilic associative polyurethane of formula (I):

(I)

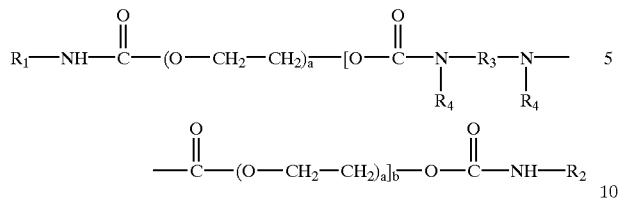

in which
at least one of the radicals $R_1$ and $R_2$ is a higher alkyl group having 8 to 18 carbons,
$R_3$ is a hydrocarbon-based radical having from 4 to 36 carbons,
$R_4$ is chosen from hydrogen and $C_1$–$C_6$ alkyl radicals,
a ranges, independently, from 90 to 600, and
b ranges from 1 to 4, and (B) at least one nonionic polymer comprising at least one unit containing a fatty chain and which is other than the polymer of formula (I), wherein (A) and (B) are added in a combined amount effective to thicken said composition.

17. A process for treating hair comprising applying to said hair a composition comprising, in a cosmetically acceptable medium:

(A) at least one nonionic amphiphilic associative polyurethane corresponding to formula (I)

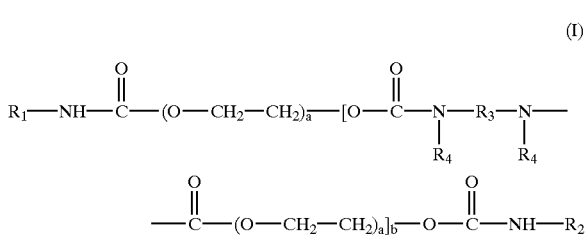

in which
at least one of the radicals $R_1$ and $R_2$ is a higher alkyl group having 8 to 18 carbons,
$R_3$ is a hydrocarbon-based radical having from 4 to 36 carbons,
$R_4$ is chosen from hydrogen and $C_1$–$C_6$ alkyl radicals,
a ranges, independently, from 90 to 600, and
b ranges from 1 to 4, and (B) at least one nonionic polymer comprising at least one unit containing a fatty chain and which is other than the polymer of formula (I), and drying the hair without rinsing said composition from the hair.

* * * * *